United States Patent [19]

Sakairi et al.

[11] Patent Number: 4,570,068
[45] Date of Patent: Feb. 11, 1986

[54] INTERFACE FOR LIQUID CHROMATOGRAPH AND MASS SPECTROMETER

[75] Inventors: Minoru Sakairi, Kokubunji; Hideki Kambara, Hachioji, both of Japan

[73] Assignee: Hitachi, Ltd., Tokyo, Japan

[21] Appl. No.: 550,973

[22] Filed: Nov. 14, 1983

[30] Foreign Application Priority Data

Nov. 17, 1982 [JP] Japan .................. 57-200440

[51] Int. Cl.⁴ .......................................... B01D 59/44
[52] U.S. Cl. ............................ 250/288; 250/423 R; 310/323
[58] Field of Search .................. 73/61.1 C; 310/323; 250/281, 288, 423 R

[56] References Cited

U.S. PATENT DOCUMENTS 4,112,297  9/1978  Miyagi et al. .............. 250/423 R
4,290,074  9/1981  Roger ......................... 310/323
4,406,405  9/1983  Marichy ...................... 310/323

*Primary Examiner*—Bruce C. Anderson
*Attorney, Agent, or Firm*—Antonelli, Terry & Wands

[57] ABSTRACT

An interface for liquid chromatograph/mass spectrometer (LC/MS) comprises a liquid chromatograph, an atomizing means for successively atomizing an effluent from the liquid chromatograph, and a mass spectrometer for mass-analyzing samples from the atomizing means, where the atomizing means comprises a conical horn and an ultrasonic vibrator. The conical horn has, along its center line, a perforation for passing the effluent. The ultrasonic vibrator is of a doughnut type and is provided around the conical horn and partly in close contact with the conical horn. Mists generated at the end of the conical horn are carried into the ion source of the mass spectrometer together with a carrier gas.

8 Claims, 3 Drawing Figures

INTERFACE FOR LIQUID CHROMATOGRAPH AND MASS SPECTROMETER

BACKGROUND OF THE INVENTION

This invention relates to an interface for a liquid chromatograph and a mass spectrometer (LC/MS), and particularly to an improvement of an interface using ultrasonic vibrator for atomizing an effluent from the liquid chromatograph (LC).

An atmospheric pressure ionization mass spectrometer (APIMS) is a mass spectrometer (MS) capable of mass analyzing trace amounts of samples by efficiently ionizing the sample at the atmospheric pressure by a corona discharge or by $\beta$-rays emitted from $^{63}$Ni. A liquid chromatograph (LC) is device capable of separating and detecting nonvolatile or thermally labile compounds and has been so far widely utilized. However, it has been tried to combine a liquid chromatograph (LC) with a mass spectrometer (MS), because no highly sensitive detector for liquid-chromatograph (LC) is available and no information is obtained as to molecular structure, such as the mass of sample, etc. [Anal. Chem. 51 682A (1979)].

Atmospheric pressure ionization mass spectrometer (APIMS) is highly sensitive and can perform ionization at the atmospheric pressure, and thus is very convenient for the desired combination with the liquid chromatograph (LC). Horning et al proposed a liquid chromatograph/atmospheric pressure ionization mass spectrometer (LC/APIMS). [Anal. Chem. 47 2369 (1975); J. Chromatogr. 99 13 (1974)]. Since then, the present inventors also proposed an interface for LC/MS, where an effluent from the liquid chromatograph (LC) is atomized by an ultrasonic vibrator and mass-analyzed in the atmospheric pressure ionization mass spectrometer (APIMS). For example, such an interface for LC/MS is disclosed in Japanese Laid-open Utility Model Publication No. 167467 (1981). FIG. 1 shows a basic structure of the interface for LC/MS, where an effluent from liquid chromatograph (LC) column 1 in a liquid chromatograph 13 is continuously supplied to the surface of an ultrasonic vibrator 9 along a guide wire 10 for the LC effluent, and atomized on the surface of the ultrasonic vibrator 9, and the resulting mists are carried into the ion source 11 of an atmospheric pressure ionization mass spectrometer (APIMS) 15 comprising the ion source 11 and an analyzer 7 together with a carrier gas from a carrier gas inlet pipe 2.

The ion source 11 comprises a heater 5 for making the mists generated by the ultrasonic vibrator 9 finer, a corona discharge electrode 6 for ionizing the samples, and an outlet pipe 8 for eliminating an excess gas. The carrier gas and samples can be efficiently ionized at the atmospheric pressure. After the ionization, ions are carried into the analyzer 7 and mass-analyzed.

In the foregoing structure, the ultrasonic vibrator 9 is used, as such, for the atomizing, and thus the volume of the interface for LC/MS 14, that is, the dead volume indicated by dotted line 12 is increased by amount corresponding to the area of ultrasonic vibrator 9.

Generally, the diffusion rate is proportional to a difference in concentration between the two sides at the boundary surface, that is, a concentration gradient, and also to a cross-section of the boundary surface at the same time. To suppress the diffusion of a substance, the cross-section of the boundary surface must be thus reduced, and the time required for passing through the boundary surface must be shortened. That is, in the interface for LC/MS 14 the diffusion rate of a substance greatly depends on volume 12 of the interface. In other words, if the volume of the interface for LC/MS is large, as indicated by dotted line 12, samples successfully separated from one another in LC column 1 will be mixed together again due to the high diffusion rate. This has been a problem in the conventional interface.

SUMMARY OF THE INVENTION

The object of the present invention is to provide an interface of LC/MS, where an ultrasonic atomizer capable of reducing a dead volume of an interface is provided.

The said object can be attained by an interface for LC/MS, which comprises a liquid chromatograph (LC), an ultrasonic atomizer for successively atomizing an effluent from the liquid chromatograph (LC), and a mass spectrometer (MS) for mass-analyzing samples, wherein the ultrasonic atomizer comprises a conical horn having a perforation for guiding the effluent from the liquid chromatograph (LC) and an ultrasonic vibrator provided in close contact with the conical horn.

With the structure of the present interface, the effluent can be atomized at the end of the conical horn, and thus the dead volume of the interface between the liquid chromatograph and the mass spectrometer can be reduced to 1/10 of the conventional dead volume. As a result, a high performance interface can be provided, where the prior art problem that samples separated from one another in the LC column are mixed together again by diffusion in the interface has been completely solved.

DETAILED DESCRIPTION OF THE PREFERRED EMBODIMENT

Figure 1:
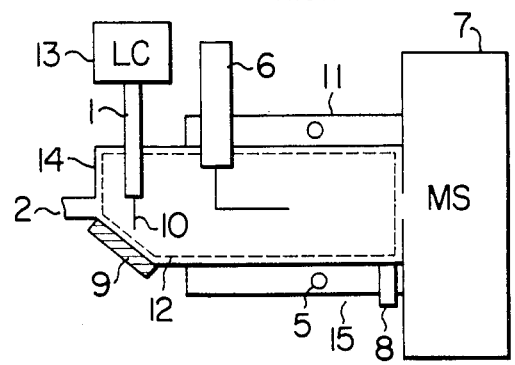
FIG. 1 is a cross-sectional view of one example of the conventional interface.

The present invention will be described in detail below, referring to the drawings.

Figure 2:
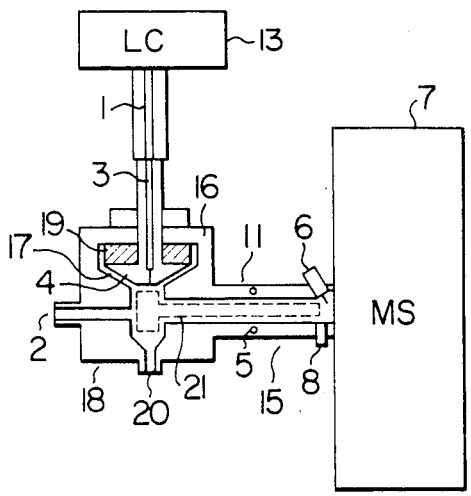
FIG. 2 is a cross-sectional view of one embodiment of the present interface.
Figure 3:
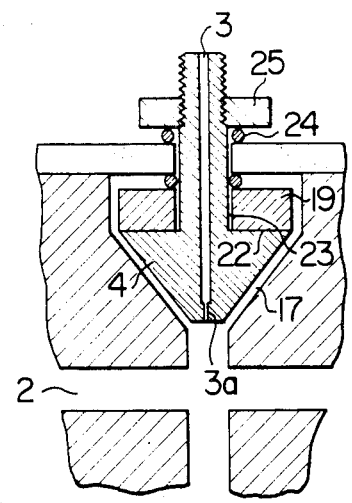
FIG. 3 is an enlarged view of a conical horn and an ultrasonic vibrator in FIG. 2.

In FIG. 2 is shown a basic structure of the interface for LC/MS according to the present invention. An effluent containing samples separated from one another in an LC column 1 in a liquid chromatograph 13 enters an interface 18 between the liquid chromatograph (LC) 13 and a mass spectrometer (MS) 15 together with a solvent. The interface 18 is provided with an ultrasonic atomizer consisting of a conical horn 4 and an ultrasonic vibrator 19. For detail, reference should be made to FIG. 3.

The conical horn 4 is made of stainless steel and has a perforation 3 along the center line, one end of the conical horn being connected to the LC column 1, and the other end being in close contact with the ultrasonic vibrator 19. The perforation 3 has a smaller inner diameter at the end 3a of conical horn 4.

The ultrasonic vibrator 9 is of a doughnut type and fixed to the conical horn 4 in a close contact. The perforation 3 runs through the ultrasonic vibrator along the center line. There is a clearance 23 between the inner peripheral side of ultrasonic vibrator 19 and the conical horn 4. The ultrasonic vibrator 19 has the following specification:

Material: zircon lead titanate
Frequency: 100 kHz
Power: 30 W

A clearance 17 is provided between the conical horn 4 and the body of the interface 18, and the conical horn is separated from the body of the interface 18 through an O ring 24, and screwed with a nut 25.

The effluent continuously supplied from the LC column 1 through the perforation 3 is fed to the end of conical horn 4 and atomized at the end by the ultrasonic vibrator 19. Mists of larger particle sizes fall downward by gravity, and are eliminated through an outlet pipe 20. On the other hand, mists of smaller particle sizes are carried into the ion source 11 of APIMS 15 with a carrier gas from a carrier gas inlet pipe 2.

In the ion source 11, the mists are further reduced in the particle size by a heater 5. The samples in the mist are efficiently ionized with the carrier gas by a needle electrode 6. Excess gas in the ion source 11 is eliminated through an outlet pipe 8. The thus ionized samples are mass-analyzed in an analyzer 7.

According to the present invention, the area at the end of conical horn 4 can be much reduced, as described above, and thus the dead volume of the interface 18 between the liquid chromatograph and the mass spectrometer can be much reduced, as indicated by dotted line 21, as compared with that of the conventional ultrasonic vibrator.

In the foregoing embodiment, a doughnut type ultrasonic vibrator is exemplified, and ultrasonic vibrators of other types can be also used in the present invention. An atmospheric pressure, ionization mass spectrometer (APIMS) is exemplified as a mass spectrometer (MS), and other types can be also used in the present invention. However, an atmospheric pressure ionization mass spectrometer (APTMS), which can perform very efficient ionization at the atmospheric pressure, is most suitable for the present invention.

As described above, the dead volume of the interface between the liquid chromatograph (LC) and the mass spectrometer (MS) can be reduced to 1/10 of that of the conventional interface according to the present invention, so that the peak width obtained in the selected ion monitoring (SIM) by the mass spectrometer can be made nearly equal to the peak width obtained by an ultraviolet detector usually used as a detector for the liquid chromatograph (LC), and a risk of remixing by diffusion of the samples separated from one another in the liquid chromatograph (LC) can be suppressed to the same extent as that attained by the ultraviolet detector.

What is claimed is:

1. An interface for liquid chromatograph and mass spectrometer, which comprises a liquid chromatograph, an ultrasonic atomizing means for successively atomizing an effluent from the liquid chromatograph, a mass spectrometer for mass-analyzing samples from the ultrasonic atomizing means, the ultrasonic atomizing means including a conical horn having a perforation for guiding the effluent from the liquid chromatograph and an ultrasonic vibrator provided in close contact with the conical horn, the ultrasonic atomizing means providing atomized mists of different particle size of the effluent in a vertically downward direction, and a carrier gas inlet means disposed adjacent to an outlet of the ultrasonic atomizing means for supplying a carrier gas in a predetermined direction transverse to the vertically downward direction of the atomized mists for carrying only atomized mists having a particle size less than a predetermined value to the mass spectrometer.

2. An interface according to claim 1, wherein the mass spectrometer comprises an ion source for ionizing the samples from the ultrasonic atomizing means, as carried by the carrier gas, and an analyzer for mass-analyzing the ions of samples generated in the ion source.

3. An interface according to claim 2, wherein the ionization is carried out at atmospheric pressure.

4. An interface according to claim 1 or 2, wherein the ultrasonic vibrator which is in close contact with the conical horn is provided, thereby atomizing the effluent at the end of the horn.

5. An interface according to claim 1 or 2, wherein the perforation has a smaller inner diameter at the end of the conical horn.

6. An interface according to claim 1 or 2, wherein the perforation extends through the conical horn in the vertically downward direction so that the conical horn is open at its vertically downward end.

7. An interface according to claim 1 or 2, wherein a means for eliminating atomized mists of larger particle size than the predetermined value is provided under an open end of the perforation at the end of the conical horn.

8. An interface according to claim 1, further comprising means disposed in the vertically downward direction of the atomized mists for eliminating atomized mists having a particle size larger than the predetermined value.

* * * * *